United States Patent
Hsu et al.

(10) Patent No.: US 7,005,144 B2
(45) Date of Patent: Feb. 28, 2006

(54) ANTLER COMPOSITION AND ITS MANUFACTURING PROCESS

(75) Inventors: David H. Hsu, Diamond Bar, CA (US); Eve Szu-Ju Chen, 23441 Golden Springs Dr., #266, Diamond Bar, CA (US) 91765

(73) Assignee: Eve Szu-Ju Chen, Diamond Bar, CA (US)

( * ) Notice: Subject to any disclaimer, the term of this patent is extended or adjusted under 35 U.S.C. 154(b) by 438 days.

(21) Appl. No.: 10/325,746

(22) Filed: Dec. 23, 2002

(65) Prior Publication Data

US 2003/0228372 A1 Dec. 11, 2003

(30) Foreign Application Priority Data

| Jun. 7, 2002 | (TW) | ................................ 91112440 A |
| Jun. 7, 2002 | (TW) | ................................ 91112441 A |
| Jun. 7, 2002 | (TW) | ................................ 91112442 A |

(51) Int. Cl.
*A61K 35/32* (2006.01)

(52) U.S. Cl. .................................................... 424/549
(58) Field of Classification Search ................. 424/549
See application file for complete search history.

(56) References Cited

U.S. PATENT DOCUMENTS 6,099,867 A * 8/2000 Sim ............................ 424/549
6,482,443 B1 * 11/2002 Lee ............................. 424/543

* cited by examiner

*Primary Examiner*—Herbert J. Lilling
(74) *Attorney, Agent, or Firm*—Bacon & Thomas, PLLC

(57) ABSTRACT

An antler composition and its manufacturing process are disclosed, the composition comprises an antler extract mixture and a matrix which comprises β-cyclodextrin, a higher ester compound, a proteinase inhibitor, and an organic solvent; wherein the weight ratio of the matrix to the antler extract mixture is between 1:1.5 and 1:2.7. The antler composition poses excellent activities and stable properties to be released steadily in human body. The present invention also relates to the antler extract mixture and the process for preparing the antler composition and the antler extract mixture.

17 Claims, No Drawings

ANTLER COMPOSITION AND ITS MANUFACTURING PROCESS

BACKGROUND OF THE INVENTION

1. Field of the Invention

The present invention relates to an antler composition and, more particularly, to an antler composition comprising a special matrix. The present invention further relates to a special antler extract mixture, and to a process to produce the antler extract mixture.

2. Description of Related Art

There are extensive amount of polymeric materials such as proteins and peptides in velvet antler extract. These polymers are said to play important roles in various function in human body, including anti-aging, boosting immune system, and anti-disease etc. Oral administration is the most popular and convenient way for taking such products, however, the nutriment may be degrade by the strong acid in our stomach, and some polymer molecules will lose their activities to lower the efficiency of velvet antler. Therefore, the non-oral administration, which delivers the active molecules into blood directly, becomes more important.

The non-oral administrations are usually nasal or sublingual administration. The most effective non-oral administration method for nutriment is the mucosa spray method, which perform good bioavailability and pharmadynamics. Because the large surface area under the tongue and intranasal areas, where has less enzymatic activity, so the degradation of polymeric material such as velvet antler is less. In addition, the spray form is very convenient and popular to consumers.

However, there are also many disadvantages for mucosa spray. For example, plenty of fluid flows through the mucus surface, therefore the time period available for the therapeutic absorption is relatively short. Another question is that the peptides or proteins with higher molecule weight are not easily adsorbed through the tongue or nasal membrane due to poor permeability. Furthermore, most medicine without coating matrix loses their activity rapidly. In order to prolong the release of therapeutic agent to 24–48 hours, the development of a suitable polymeric matrix is necessary.

Many patents in polymer matrix advocate the use of various biopolymers for the releasing control, but most of these polymers are not suitable to be used in velvet antler extract. The reasons are:

(1) There are many polymeric materials in velvet antler extract which needs a special elastic polymer with strong adsorption property to form an encapsulated complex in order to prolong the residence time of them, so as to enhance the absorption of antler extract and other gradients in the composition.

(2) The polymer complex used in an antler extract should be insoluble in water and with right size to accommodate the antler extract and other ingredients in the composition.

(3) The polymer must be pharmaceutically acceptable and free of toxicity. In addition, the final product is sterilized under high temperature and high pressure, so these ingredients must be chemically stable.

In order to enhance the permeability of the polymeric matrix and the active polymer complex in antler extract, it needs a special solvent with dual hydrophilic and hydrophobic function. Furthermore, for avoiding the degradation of the active factor in antler extract, the proteinase activity should be inhibited. Therefore, an enzymatic inhibitor should be added to the composition.

U.S. Pat. No. 4,702,923 discloses a yogurt composition with 7–15% velvet antler powder enriched. The yogurt composition is considered inferior in medicinal value because the low content of antler powder. Because there are many polymers in velvet antler extract, the antler extract becomes water-insoluble when the amount of antler extract is high. So the antler composition comprising high amount of antler extract is usually hard to be packed as solution or spray, and it confines the application of aqueous antler composition. Therefore, products comprising high amount of velvet antler has not been developed in the market.

In traditional method, the active compound of velvet antler was obtained by extracting with alcohol or water, and then lyophilizing the active compound and grounding into powder. But this method cannot afford high quality and quantity active compound and costs a lot. U.S. Pat. No. 6,099,867 teaches a new processing method to heat the velvet antler at 100 to 120° C. for 2 hour, then go through several steps of separation, homogenization, filtering, mixing, and lyophilization. This method includes severe heating for extended time, and it ineluctably triggers chemical reactions which could significantly reduce the medicinal value of velvet antlers.

Therefore, it is desirable to provide a novel antler composition and producing method to mitigate and/or obviate the aforementioned problems.

SUMMARY OF THE INVENTION

The object of the present invention is to provide an antler composition which is parenteral and released steadily.

Another subject of the present invention is to provide a novel process for producing the antler composition which comprising active compounds encapsulated in a matrix.

Another subject of the present invention is to provide a novel antler composition comprising high quality and quantity antler extract, which is obtained by addition of special additives and special process. The composition keeps water-soluble for a long period to maintain stability of the active compound therein.

To achieve the object, the antler extract mixture of the present invention comprises 70 to 90 wt % of velvet antler powder, 2 to 10 wt % of amino acid, 1 to 5 wt % of carbohydrate, 0.1 to 2 wt % of vitamin, 0.1 to 3 wt % of minerals. Said antler extract mixture can optionally comprises 0.1 to 1.5 wt % of emulsifier, 0.1 to 1.0 wt % of stabilizer, and 0.005 to 0.2 wt % additive.

To achieve another object, the antler composition of the present invention comprises an antler extract mixture and a matrix which comprises β-cyclodextrin, a higher ester compound, a proteinase inhibitor, and an organic solvent; wherein the weight ratio of said matrix to said antler extract mixture is between 1:1.5 and 1:2.7. Said weight ratio of β-cyclodextrin to said higher ester compound to said proteinase inhibitor to said organic solvent is between 1:0.01: 0.02:0.45 and 1:0.20:0.18:0.55. Said antler mixture has been described above.

Other objects, advantages, and novel features of the invention will become more apparent from the following detailed description.

DETAILED DESCRIPTION OF THE PREFERRED EMBODIMENT

The main purpose of the present invention is to provide a novel antler composition and the method for producing it. The antler composition comprises an antler extract mixture and a matrix which comprises β-cyclodextrin, a higher ester compound, a proteinase inhibitor, and an organic solvent. Preferably, the weight ratio of β-cyclodextrin to said higher ester compound to said proteinase inhibitor to said organic solvent is between 1:0.01:0.02:0.45 and 1:0.20:0.18:0.55, and the weight ratio of said matrix to said antler extract mixture is between 1:1.5 and 1:2.7. All materials used in the present invention are all pharmaceutically acceptable.

Preferably, the higher ester compound mentioned above is obtained by reacting alcohol with 12 to 18 carbon atoms and carboxylic acid with 8 to 18 carbon atoms while said proteinase inhibitor is mucus proteinase inhibitor, and said organic solvent is propylene glycol.

The antler composition is produced by the following steps: (a) mixing said β-cyclodextrin, said higher ester compound, said proteinase inhibitor, and said organic solvent with a specific ratio mentioned above, (b) then adding the mixture into pure water wherein the preferable weight ratio of the mixture to the water is 1:3, and blending the mixture at room temperature for 18 to 36 h to form a suspension comprising the matrix; (c) adding the antler extract mixture aforementioned to the suspension and keep agitating the suspension with low speed at room temperature for about 18 to 24 hour until microcapsules performs, (d) subsequently incubating the mixture at 4° C. for 24 to 48 hour until the precipitate forms, and finally (e) filtering obtained mixture to get the precipitate. The step (d) can be repeated three or four times and the precipitate can be washed by cold water. The final precipitate can be optionally added into three fold of pure water, and the mixture is mixed in a homomixer for about 15 to 20 minutes until it is homogenized. The homogenized mixture is then disinfected and packed with a spray aerosol or pulverized into powder for longtime storage. The whole packing process is sterile and the package is suitable for nasal or sublingual delivery.

As mentioned above, velvet antlers contain many water-insoluble polymers so that conventional antler composition comprises only low amount of antler extract. Therefore, the present invention offers an emulsification method to dissolve this problem. Accordingly, the antler extract mixture comprises two parts: one is antler mixture and the other part is emulsifying part.

The antler mixture contains 70 to 90 wt % of velvet antler powder, 2 to 10 wt % of amino acid, 1 to 5 wt % of carbohydrate, 0.1 to 2 wt % of vitamin, and 0.1 to 3 wt % of minerals. All contents are provided as powder and mixed well. The emulsifying part comprises 0.1 to 1.5 wt % of emulsifier, 0.1 to 1.0 wt % of stabilizer, and 0.005 to 0.2 wt % additive.

Preferably, the antler powder is lyophilized antler powder; and one or more amino acids are selected from alanine, arginine, asparigine, aspartic acid, cystine, glutamine, glutamic acid, glycine, histidine, isoleucine, leucine, lysine, methionine, phenylalanine, proline, serine, threonine, tryptophan, tyrosine, or valine. In addition, one or more fatty acids preferably select from the group consisted of stearic acid, oleic acid, linoleic acid, lauric acid, caprylic acid, capric acid, myristic acid, or palmitic acid; and one or more carbohydrates preferably select from the group consisted of starch, maltose, fructose, sucrose, glucose, sorbitol, arabinose, xylose, lactose, corn syrup solid, maltodextrins, dextrine, and dextrose. One or more vitamins preferably select from vitamin A, vitamin $B_1$, vitamin $B_2$, vitamin $B_6$, vitamin $B_{12}$, vitamin C, vitamin D, vitamin E, vitamin K, folic acid, biotin, or pantothenic acid; and one or more minerals preferably select from zinc, calcium, phosphorus, potassium, cobalt, manganese, iron, copper, sodium, magnesium, iodine, chlorine, or fluorine.

Preferably, one or more emulsifiers select from Mono and Diglycerides, Sorbitan, Monostearate, Polysorbate 60, Polysorbate 80, Lecithin, Emplex, Caprol, or Myyerol; and one or more stablizers select from Xanthan gum, CMC gum, Carageenan, Methocol, Klucel, Guar gum, Locus bean gum, and Alginates. One or more additives select from the buffering agent, sequestraut, preservative, or food pigment; wherein said buffering agent is potassium phosphate and/or sodium phosphate; said sequestraut is EDTA, citric acid, and/or polyphosphate; said preservative is potassium propionate and/or potassium sorbate; and said food pigment selects is yellow No. 5, yellow No. 6, red No. 2, red No. 40, or β-carotene.

The antler extract mixture of the present invention is prepared as the following steps: (a) adding 70 to 80° C. hot water to said antler extract mixture in a mixer speed and agitating with high at 60° C. for 10 minutes; (b) subsequently adding said emulsifying agents to the mixture, heating at 50 to 70° C. for 10 to 20 minutes, and mixing well; (c) subjecting the mixture obtained from step (b) in another mixture, mixing well with low speed and heating at 60 to 65° C. for 30 minutes; (d) degassing the mixture with a vacuum pump and repeating for one to four times until the foams are disappeared; (e) homogenizing said mixture under the pressure between 1,000 and 1,500 psi followed by under the pressure between 1,500 and 3,000 psi to form an emulsified mixture; (f) chilling the emulsified mixture to 3 to 6° C. rapidly wherein the chilling process is preferably a HTST chilling process; and finally (g) transferring the cool emulsified mixture to an maturing vat and agitating the mixture with low speed at 4° C. for 24 hour to complete the degassing and maturing process. The obtained products are homogenized and degassing thoroughly, and stored in a cold plastic bottle. Said "mature" step indicates that the mixture is mixed well and incubated until the all reactions occurring in the mixture reach equilibrium.

The velvet antler powder contained in the antler extract mixture is prepared by soaking the antler in hot water wherein the water temperature is preferably between 80 and 90° C., and more preferably, 85° C.; after 30 minutes, separating the skin part and the other tissue part; then homogenizing said skin part and tissue part separately and removing the hair portion from the homogenized skin part subsequently. Next, to recombine said homogenized skin part and said tissue part to obtain a suspension, and then separate the water-soluble and water-insoluble parts of the suspension. Finally, pulverize said water-insoluble part and said water-insoluble part into powder in a fluidized bed dryer with an temperature between 75 and 90° C., wherein the temperature of the fluidized bed dryer is between 70 and 95° C., and preferably, 60 and 85° C. to obtain an antler powder which contains water less than 6%. In one embodiment, the water-insoluble portion is dried in an agitated swirl fluidized bed dryer at 60 to 85° C., and the obtained powder contains only 7% of water. The powder from water-soluble part and that from water-insoluble part can be used together or separately.

The present invention will be further illustrated by the following examples.

EXAMPLE 1

Preparation of Velvet Antler Powder

The frozen deer antlers were cut into 5 cm long strips by using electric saw. The antler strips were then cleaned in warm water and soaked in 65° C. water for 30 minutes. The skin part was then separated from other tissue parts.

The antler skin was homogenized in a Waring blender at high speed for 5 minutes, the skin homogenate was then filtered through three layers of cheesecloth, and the filtrate was washed with some distilled water. The hair portion was discarded. The other tissue parts of deer antler were gone through the same homogenization and filtration steps as above.

The two filtrates were combined and homogenized in Waring blender at high speed for another 5 minutes. The combined homogenate was then centrifuged at 1000×g for 15 minutes. Both the supernatant and precipitate were separately dried. The supernatant portion (water-soluble part) was placed in a fluidized bed dryer, and dried for 20 minutes with an outlet temperature of 80° C., and the resulting solid contains water less than 7%. The precipitate portion (water-insoluble part) was placed in an agitated swirl fluidized bed dryer, and dried for 20 minutes with an outlet temperature of 78° C. and the resulting solid contains water less than 6%. The resulting solids were then pulverized into fine powder and mixed well.

EXAMPLE 2

Preparation of the Antler Extract Mixture

A. The formula of the antler mixture lists below:
B.

TABLE 1

| Material | % (W/W) | Weight (g) |
|---|---|---|
| Velvet antler | 86.495 | 864.95 |
| Lysine | 0.500 | 5.00 |
| Histidine | 0.400 | 4.00 |
| Proline | 0.800 | 8.00 |
| Tryptophan | 0.400 | 4.00 |
| Isoleucine | 0.300 | 3.00 |
| Leucine | 0.500 | 5.00 |
| Threonine | 0.600 | 6.00 |
| Methionine | 0.200 | 2.00 |
| Arginine | 0.800 | 8.00 |
| Phenylalanine | 0.600 | 6.00 |
| Stearic acid | 0.700 | 7.00 |
| Oleic acid | 0.800 | 8.00 |
| Linoleic acid | 0.800 | 8.00 |
| Lauric acid | 0.800 | 8.00 |
| Palmitic acid | 0.900 | 9.00 |
| Corn syrup solid | 1.500 | 5.00 |
| Lactose | 0.500 | 5.00 |
| Glucose | 0.500 | 5.00 |
| Dextrose | 0.500 | 5.00 |
| Ascorbic acid | 0.500 | 5.00 |
| Calcium carbonate | 0.800 | 8.00 |
| Magnesium oxide | 0.100 | 1.00 |
| Zinc oxide | 0.005 | 0.05 |
| Total | 100.00 | 1,000.00 |

(Sample No.: AE-792)
* All amino acids in this formula are essential amino acids.

C. The formula of the emulsifying agents listed below:

TABLE 2

| Materials | % (W/W) | Weight (Kg) |
|---|---|---|
| Antler extract sample No. AE-792 | 69.37 | 69.37 |
| Distilled water (80° C.) | 30.00 | 30.00 |
| Lecithin | 0.08 | 0.08 |
| Mono-glyceride | 0.03 | 0.03 |
| Di-glyceride | 0.01 | 0.01 |
| Sorbitan monoglycerate | 0.10 | 0.10 |
| Carageenan GP-713 | 0.10 | 0.10 |
| Xanthan gum (Kelco) | 0.04 | 0.04 |
| Potassium phosphate | 0.10 | 0.10 |
| Salts | 0.15 | 0.15 |
| β- Carotene | 0.02 | 0.02 |

(Sample No. HL-483)

The contents mentioned above were added in a mixer and mixed with high speed as the steps of: (1) adding the 80° C. distilled water; (2) adding the lecithin, mono-glyceride, di-glyceride, and sorbitan monoglycerate slowly into the warm water; (3) adding potassium phosphate into the mixture above subsequently; (4) adding Carageenan GP-713 followed by adding Xanthan gum which is dissolved in propylene glycol with the weight ratio of 1:10; (5) adding salts and β-carotene to the mixture above; and (6) finally adding the antler extract mixture AE-792 to said mixture.

All contents mentioned above were placing in a mixer and agitated with high speed for 10 minutes, and the mixture was then transferred to another mixer and agitated with mediate speed at 60° C. for about 30 minutes. All the solid contents were evaluated to confirm the formula. After heating, the mixture was drawn to a deaerator by a vacuum pump and deaerated for four times for eliminating foam. After foam eliminated, the mixture was transferred in a homogenizer for homogenizing under 1,200 psi followed by homogenizing under 3,500 psi to emulsify the mixture, wherein the emulsification was carried out at about 55° C.

After complete emulsification, the mixture was transferred in an cooler for rapid cooling to 4° C., and transferred in an maturing vat. Agitate the mixture with low speed to deaerate for maintaining the homogenized state of the mixture, and keep it at 4° C. for storage.

Store the suspension obtained from aforementioned treatments in a sterile bottle and refrigerate it for a long time to observe the stability of the suspension. After five months, surprisingly, only 1% of the suspension performs water-insoluble. This indicates that the stability of suspension diluted to one tenth can reaches to 99%, and the shelf life is about 6 months.

EXAMPLE 3

Preparation of the Antler Composition

The formula of the antler composition lists below:

TABLE 3

| Contents | Weight (Kgw) |
|---|---|
| β-cyclodextrin | 6.18 |
| Sec-Butyl-3-pentaoate | 0.916 |
| Mucus proteinase inhibitor | 0.124 |
| Propylene glycol | 2.78 |
| Total | 10.00 |

The contents on table 3 were added in 30 Kg of distilled water, and the mixture was then agitated with low speed for 18 to 36 hour to form a suspension contained the matrix. 5.5 Kg of antler extract mixture (HL-483) was added into the suspension, and the mixture was agitated with low speed at room temperature for 18 to 24 hour until the microcapsules performs. The obtained mixture was incubated at 4° C. to form precipitates followed by filtering off the mixture, and the solid filtrates was washed with distilled water for three times. The final solid product was about 18 Kg, and it is added into 55 Kg of distilled water in a homomixer to stir for 15 minutes. After mixing well, the mixture was heated dramatically at 212° F. for about 2 minutes, then chilled to 4° C. and stored in a sterile glass bottle attached an aerator. The whole processing processes were disinfected.

EXAMPLE 4

Storage Test of the Antler Composition

The antler composition produced from the steps of example 2 was compared with the following comparative examples in stabilities

Comparative Example 1

All the contents in comparative example 1 are the same as example 2 (HL 483), and the producing steps are also similar to example 2, except that the antler mixture (AE-792) is added into distilled water first and then the lecithin and amino acids are added to the mixture.

Comparative Example 2

All the contents in comparative example 2 are the same as example 2 (HL 483), and the producing steps are also similar to example 2, except that the heating step is heated at 80° C. for 30 minutes.

Comparative Example 3

All the contents in comparative example 3 are the same as example 2 (HL 483), and the producing steps are also similar to example 2, except that the aerating step is omitted.

Comparative Example 4

All the contents in comparative example 4 are the same as example 2 (HL 483), and the producing steps are also similar to example 2, except that the emulsifying step is carried out under the pressure of 500 psi followed by under the pressure of 2,000 psi.

Comparative Example 5

All the contents in comparative example 5 are the same as example 2 (HL 483), and the producing steps are also similar to example 2, except that the emulsifying step is carried out under the pressure of 1,000 psi followed by under the pressure of 2,500 psi.

Comparative Example 6

All the contents in comparative example 6 are the same as example 2 (HL 483), and the producing steps are also similar to example 2, except that the heating step is heated at 80° C. for 30 minutes.

Comparative Example 7

All the contents in comparative example 7 are the same as example 2 (HL 483), and the producing steps are also similar to example 2, except that the deaeration step is only repeated once.

Comparative Example 8

All the contents in comparative example 8 are the same as example 2 (HL 483), and the producing steps are also similar to example 2, except that the emulsifying step is carried out at 45° C.

Comparative Example 9

All the contents in comparative example 9 are the same as example 2 (HL 483), and the producing steps are also similar to example 2, except that the emulsifying step is carried out at 65° C.

Comparative Example 10

All the contents in comparative example 7 are the same as example 2 (HL 483), and the producing steps are also similar to example 2, except that the maturing step is omitted.

The samples mentioned above were incubating at room temperature and observed the water-insolubility for six months. The results list below:

TABLE 4

| | The percentage of hydrophobious portion to whole weight. | | | | | |
|---|---|---|---|---|---|---|
| | Month 1 | Month 2 | Month 3 | Month 4 | Month 5 | Month 6 |
| Example 2 | 0 | 0 | 0 | 0 | 1 | 1 |
| Comparative example 1 | 26 | 29 | 30 | 33 | 36 | 45 |
| Comparative example 2 | 5 | 7 | 7 | 7 | 8 | 8 |
| Comparative example 3 | 17 | 20 | 26 | 26 | 28 | 32 |
| Comparative example 4 | 45 | 59 | 62 | 64 | 64 | 65 |
| Comparative example 5 | 27 | 28 | 29 | 29 | 31 | 34 |
| Comparative example 6 | 4 | 5 | 6 | 6 | 7 | 8 |

TABLE 4-continued

The percentage of hydrophobious portion to whole weight.

|  | Month 1 | Month 2 | Month 3 | Month 4 | Month 5 | Month 6 |
|---|---|---|---|---|---|---|
| Comparative example 7 | 11 | 14 | 21 | 21 | 23 | 24 |
| Comparative example 8 | 47 | 50 | 53 | 53 | 54 | 56 |
| Comparative example 9 | 33 | 33 | 33 | 35 | 35 | 36 |
| Comparative example 10 | 71 | 72 | 73 | 73 | 75 | 76 |

TABLE 5

The percentage of water-insoluble portion to whole weight.

|  | Month 1 | Month 2 | Month 3 | Month 4 | Month 5 | Month 6 |
|---|---|---|---|---|---|---|
| Examle 2 | 0 | 0 | 0 | 0 | 0 | 1 |
| Comparative example 1 | 62 | 62 | 62 | 62 | 63 | 63 |
| Comparative example 2 | 100 | 100 | 100 | 100 | 100 | 100 |
| Comparative example 3 | 58 | 59 | 59 | 59 | 59 | 60 |
| Comparative example 4 | 100 | 100 | 100 | 100 | 100 | 100 |
| Comparative example 5 | 95 | 96 | 96 | 96 | 96 | 96 |
| Comparative example 6 | 100 | 100 | 100 | 100 | 100 | 100 |
| Comparative example 7 | 47 | 48 | 48 | 51 | 51 | 51 |
| Comparative example 8 | 0 | 0 | 0 | 0 | 1 | 2 |
| Comparative example 9 | 0 | 0 | 0 | 1 | 2 | 3 |
| Comparative example 10 | 0 | 0 | 4 | 4 | 4 | 5 |

The results suggest that the adding sequence of the antler mixture (comparative example 1), the temperature (comparative example 2), the frequency of deaeration (comparative example 3 and 7), the emulsifying pressure (comparative example 4 and 5), and maturing step (comparative example 10) are important factors which influence the hydorphilicity or water-solubility of the antler composition strongly. People who are skilled in this field know that the hydrophilicity and the water-solubility determine the bioavailibility and the potency of the composition. Therefore, the present invention provides a novel and special process to produce a stable and homogenized antler liquid composition contained high amount the antler.

EXAMPLE 5

The Effects of the Antler Composition on Animal Model

The effects of the traditional antler compositions on rats are compared with the antler composition of the present invention. The rats of experimental group is feed with the antler composition of the present invention while the rats of the comparative group is feed with the traditional antler composition. The control group is feed with the normal feed. Said traditional antler composition comprises 20 g of conventional antler power, 10 g of Herba Corydalis Bungeanae, 3 g of Squama Manitis, 4 g of Radix Scutellariae, 4 g of Curcuma aromatica salisp, 4 g of Semen Vaccariae, 4 g of Liquoric Root, 5 g of Japanese Honeysuckle Stem, 5 g of Fructus Forsythiae, 5 g of Angelica, 5 g of Red Paeony Root, 5 g of Gardenia jasminoides, 5 g of Nutgrass Galingale Rhizome, 5 g of Uniflower Swisscentaury Root. Said mixture is extracted by three fold boiling water. Said extract and the antler composition of the present invention were evaluated by the following experiments.

Experiment A The Growth State of Rats

The effects of sample HL-483 on the growth state of rats is compared with traditional lyophilized antler composition. 60 six week-old Wistar male rats whose weights are about 100 g are treated with these samples. The rats are arranged in cages, and each cage accommodates 4–6 rats. The rats are feed with distilled water and Adlibitum, a purified casein.

The samples are added in the daily feed with a dosage of 200 mg separately. The results list as table 6:

TABLE 6

The influence of different antler compositions on growth state of rats. (All data are average values)

| Weight (g/)/Duration | Week 0 | Week 1 | Week 2 | Week 3 | Week 4 | Week 5 | Week 6 |
|---|---|---|---|---|---|---|---|
| Control group | 100.0 | 102.3 | 104.7 | 105.3 | 107.7 | 108.1 | 109 |
| HL-483 | 100.0 | 105.3 | 106.2 | 108.4 | 110.8 | 113.4 | 114.2 |
| Traditional antler composition | 100.0 | 102.2 | 104.7 | 104.9 | 106.7 | 108.7 | 109.3 |

The results suggest that the antler composition of the present invention (HL-483) can benefit the rats' growth state.

Experiment B The Anti-Aging Effects on Rats

The sample and experimental condition are all the same as experiment A except the rats are feed with distilled water and Adlibitum, a purified casein. The samples are added in the daily feed with a dosage of 200 mg separately. The results list as table 7 and 8:

TABLE 7

The influence of different antler compositions on rat's testosterone concentration. (All data are average values)

| Groups | Concentration of testosterone (pg/100 1 plasma) |
|---|---|
| Control group | 42 |
| HL-483 (example 2) | 95 |
| Conventional antler composition | 71 |

* The anti-aging effect increases when the testosterone concentration decreases.

TABLE 8

The influence of different antler compositions on rat's MAO-B activities. (All data are average values)

| | Activity of MAO-B * | |
|---|---|---|
| Groups | Liver | Barin |
| Control group | 5.7 | 2.4 |
| HL-483 (example 2) | 2.5 | 0.5 |
| Conventional antler composition | 4.3 | 1.3 |

* The anti-aging effect increases when the activity of MAO-B decreases.

The results suggest that the anti-aging effect of IL-483 is much better than that of conventional antler composition.

Experiment C The Anti-Inflaming Effects on Rats

The sample and experimental condition are all the same as experiment A except the rats of control group are feed with conventional antler composition. The samples are added in the daily feed with a dosage of 200 mg separately. The results list as table 9:

TABLE 9

The influence of different antler compositions on rat's leukocyte numbers. (All data are average values)

| | Number of rat leukocyte */ ml × $10^{-5}$ |
|---|---|
| Control group | 36 |
| HL-483 | 6 |
| Conventional antler composition | 17 |

*The anti-inflaming effect increases when the number of leukocyte decreases.

The results suggest that the anti-aging effect of HL-483 is much better than that of conventional antler composition.

EXAMPLE 6

Pharmaco-Kinetics Study of the Antler Composition Comprising the Matrix

The present experiment will study the effects of the administration way on the bioavalibility of the antler composition of the present invention. The conventional antler composition was a powdered mixture which packed in a capsule and was delivered by oral administration, while the antler composition of the present invention was delivered by spray.

Human growth hormone (HGH), which is abundant and stable in antler composition, is a marker representing the active compounds in antler composition. So we compare the HGH amount of various samples to determine the effects of different administration way.

Experiment A In Vitro Releasing Rate of the Antler Composition in the Present Invention The antler composition capsule without polymer matrix (control group) is compared with the antler composition of the present invention wherein the weight ratio of the antler extract to the β-cyclodextrin lists in table 10:

TABLE 10

The weight ratio of the antler mixture to the β-cyclodextrin

| Group | Weight part of antler extract | Weight part of β-cyclodextrin |
|---|---|---|
| Group 1 | 1 | 1 |
| Group 2 | 1 | 1.5 |
| Group 3 | 1 | 2.0 |
| Group 4 | 1 | 2.7 |
| Group 5 | 1 | 3.5 |

The samples mentioned above all comprise 150 mg of HGH, which is determined by IRMA (RADZM Co.). Other components are the same as example 1.

The mixture mentioned above is put into a vial containing 10 ml of PBS buffer and stirred steadily. After 24 hours, the mixtures are transferred to another vial for the HGH amount analyzation. Repeat these steps until 144 hour. The results list as table 11:

TABLE 11

The HGH amount in antler composition changes by time

| Time (h) | Control group | Group 1 | Group 2 | Group 3 | Group 4 | Group 5 |
|---|---|---|---|---|---|---|
| 0 | 150 | 150 | 150 | 150 | 150 | 150 |
| 24 | 35 | 75 | 135 | 129 | 123 | 98 |
| 48 | 12 | 54 | 114 | 107 | 109 | 73 |
| 72 | 0 | 17 | 80 | 81 | 77 | 28 |
| 96 | 0 | 3 | 56 | 52 | 53 | 9 |
| 120 | 0 | 0 | 32 | 27 | 25 | 0 |
| 144 | 0 | 0 | 4 | 5 | 2 | 0 |

The results suggest that the releasing state of group 2 and group 4 are better than other groups.

Experiment B In Vivo Releasing Rate of the Antler Composition of the Present Invention in Human Body The treatment and the experimental conditions are similar to experiment A, but the antler composition is packed in a bottle with an aerosol. The experimental group was sublingual administration while the control group was oral administration. The weight ratios of the antler mixture to the β-cyclodextrin are as table 12:

TABLE 12

The weight ratio of the antler mixture to the β-cyclodextrin

| Group | Weight part of antler extract | Weight part of Group β-cyclodextrin |
|---|---|---|
| Group 1 | 1 | 1 |
| Group 2 | 1 | 1.5 |
| Group 3 | 1 | 2.0 |
| Group 4 | 1 | 2.7 |
| Group 5 | 1 | 3.5 |

The samples mentioned above all comprise 150 mg of HGH, which is determined by IRMA (RADZM Co.). Other components are the same as example 3.

The mixture mentioned above is put into a vial containing 10 ml of PBS buffer and stirred steadily. After 24 hours, the mixtures are transferred to another vial to analyze the HGH amount. Repeat these steps until 144 hour. The results list as table 13:

TABLE 13

The HGH amount in antler composition changes by time

| Time (h) | Control group | Group 1 | Group 2 | Group 3 | Group 4 | Group 5 |
|---|---|---|---|---|---|---|
| 0 | 150 | 150 | 150 | 150 | 150 | 150 |
| 24 | 23 | 105 | 127 | 132 | 130 | 112 |
| 48 | 0 | 83 | 109 | 115 | 117 | 87 |
| 72 | 0 | 50 | 81 | 87 | 89 | 62 |
| 96 | 0 | 17* | 52* | 59 | 58 | 24 |
| 120 | 0 | 0 | 29 | 33 | 37 | 3 |
| 144 | 0 | 0 | 3 | 5 | 9 | 0 |

*These groups are not patent in statistics ($p > 0.05$).

The results suggest that the releasing state of group 2 and group 4 are better than other groups, so the weight ratio of antler extract to matrix is preferred in the range of 1:1.5 to 1:2.7. In addition, the antler composition of the present invention can release steadily and be stable in human body for six days.

From the descriptions mentioned above, it is known that the antler composition of the present invention absorbed nasally or sublingually comprises contact active compounds. The present invention provides a matrix containing β-dextrin, which is elastic, water-soluble and non-toxic. Furthermore, the present invention provides a proper ratio of said polymers, which is suitable to pack the antler extract into microcapsules and optimize the pore size (2 to 10 micrometer) of the microcapsules. So the matrix of the present invention has a good performance of releasing the antler composition packed in the microcapsules into blood, thus maintains the potency until 24 to 48 hours. In addition, for improving the permeability of the matrix, the present invention provides a new formula which contains propyl ethylene, a stable and non-toxic solvent suitable for using in antler composition. It is deserved to notice that composition of the present invention also comprises higher ester and mucus proteinase inhibitor, which inhibit the proteinase efficiently, and thus protect the active compound in the antler composition and keep the stability of the matrix.

For comparing with the traditional antler composition for oral administration or nasal or sublingual delivery, the antler composition of the present invention can provide more active compounds, prolong the potency, and improve the permeability, thus improve the bioavalibility and release the active compounds steadily. This is what the prior art cannot achieve.

Although the present invention has been explained in relation to its preferred embodiment, it is to be understood that many other possible modifications and variations can be made without departing from the scope of the invention as hereinafter claimed.

What is claimed is:

1. An antler extract mixture, comprising 70 to 90 wt % of velvet antler powder, 2 to 10 wt % of amino acid, 1 to 5 wt % of carbohydrate, 0.1 to 2 wt % of vitamin, and 0.1 to 3 wt % of minerals.

2. The antler extract mixture according to claim 1, further comprising 0.1 to 1.5 wt % of emulsifier, 0.1 to 1.0 wt % of stabilizer, and 0.005 to 0.2 wt % additive.

3. The antler extract mixture according to claim 2, wherein said mixture is produced by the following steps:
(a) providing an antler extract mixture comprising 70 to 90 wt % of velvet antler powder, 2 to 10 wt % of amino acid, 1 to 5 wt % of carbohydrate, 0.1 to 2 wt % of vitamin, and 0.1 to 3 wt % of minerals;

(b) adding 70 to 80° C. of pure water, 0.1 to 1.5 wt % of emulsifier, 0.1 to 1.0 wt % of stabilizer, and 0.005 to 0.2 wt % additive to said powder mixture in a high speed blender, mixing well and heating at 50 to 70° C. for 10 to 20 min, wherein the weight ratio of said powder mixture to said pure water is between 1:1.5 and 1:8.0;

(c) subjecting the mixture obtained from step (b) in a blender, mixing the mixture well and heating the mixture at 60 to 65° C. for 30 min;

(d) transferring said mixture obtained from step (c) in a vacuum apparatus to degas;

(e) homogenizing said mixture obtained from step (d) followed by chilling the mixture to 4° C. rapidly; and (f) transferring said mixture obtained from step (e) in an maturing vat, stirring gently at 4° C. for 12 to 24 h to complete the degassing and maturing process.

4. The antler extract mixture according to claim 3, wherein said homogenizing process in step (e) comprising homogenizing said mixture under the pressure between 1,000 and 1,500 psi followed by homogenizing said mixture under the pressure between 1,500 and 3,000 psi; and said chilling process is a HTST chilling process.

5. The antler extract mixture according to claim 1, wherein the antler powder is lyophilized antler powder; and at least one amino acid selects from the group consisted of alanine, arginine, asparigine, aspartic acid, cystine, glutamine, glutamic acid, glycine, histidine, isoleucine, leucine, lysine, methionine, phenylalanine, proline, serine, threonine, tryptophan, tyrosine, and valine.

6. The antler extract mixture according to claim 1, wherein at least one fatty acid selects from the group consisted of stearic acid, oleic acid, linoleic acid, lauric acid, caprylic acid, capric acid, myristic acid, palmitic acid; and at least one carbohydrate selects from the group consisted of starch, maltose, fructose, sucrose, glucose, sorbitol, arabinose, xylose, lactose, corn syrup solid, maltodextrins, dextrine, and dextrose.

7. The antler extract mixture according to claim 1, wherein at least one vitamin selects from the group consisted of vitamin A, vitamin $B_1$, vitamin $B_2$, vitamin $B_6$, vitamin $B_{12}$, vitamin C, vitamin D, vitamin E, vitamin K, folic acid, biotin, and pantothenic acid; and at least one mineral selects from the group consisted of zinc, calcium, phosphorus, potassium, manganese, cobalt, iron, copper, sodium, magnesium, iodine, chlorine, and fluorine.

8. The antler extract mixture according to claim 1, wherein at least one emulsifier selects from the group consisted of Mono and Diglycerides, Sorbitan, Monostearate, Polysorbate 60, Polysorbate 80, Lecithin, Emplex, Caprol, Myyerol; and at least one stablizer selects from the group consisted of Xanthan gum, CMC gum, Carageenan, Methocol, Klucel, Guar gum, Locus bean gum, and Alginates.

9. The antler extract mixture according to claim 1, wherein at least one additive selects from the group consisted of buffering agent, sequestraut, preservative, and food pigment; wherein said buffering agent is potassium phosphate and/or sodium phosphate; said sequestraut is EDTA, citric acid, and/or polyphosphate; said preservative is potassium propionate and/or potassium sorbate; and said food pigment selects from the group consisted of yellow No. 5, yellow No. 6, red No. 2, red No. 40, and β-carotene.

10. The antler extract mixture according to claim 1, wherein said velvet antler powder is produced by the following steps:
(a) soaking velvet antlers in pure hot water at 80 to 90° C. for 30 min and separating the skin part and the other tissue part;
(b) homogenizing said skin part and tissue part separately;
(c) removing the hair portion from the homogenized skin part;
(d) recombining said homogenized skin part and said tissue part;
(e) separating the water-soluble and water-insoluble parts; and
(f) pulverizing said water-insoluble part and said water-insoluble part into powder in a fluidized bed dryer with an temperature between 75 and 90° C.

11. The antler extract mixture according to claim 10, wherein the step (b) further comprising pulverizing said water-insoluble part in a fluidized bed dryer, and drying of the water-insoluble portion in an agitated swirl fluidized bed dryer.

12. An antler compositions comprising an antler extract mixture, and a matrix which comprises β-cyclodextrin, a higher ester compound, a proteinase inhibitor, and an organic solvent; wherein said antler extract mixture includes 70 to 90 wt % of velvet antler powder, 2 to 10 wt % of amino acid, 1 to 5 wt % of carbohydrate, 0.1 to 2 wt % of vitamin, and 0.1 to 3 wt % of minerals; and the weight ratio of said matrix to said antler extract mixture is between 1:1.5 and 1:2.7.

13. The antler composition according to claim 12, wherein the weight ratio of β-cyclodextrin to said higher ester compound to said proteinase inhibitor to said organic solvent is between 1:0.01:0.02:0.45 and 1:0.20:0.18:0.55.

14. The antler composition according to claim 12, wherein β-cyclodextrin is pharmaceutical acceptable β-cyclodextrin, said higher ester compound is obtained by reacting alcohol with 12 to 18 carbon atoms and carboxylic acid with 8 to 18 carbon atoms, said proteinase inhibitor is mucus proteinase inhibitor, and said organic solvent is propylene glycol.

15. The antler composition according to claim 12, wherein the product is sterilized and packed with an aerosol and is suitable for nasal or sublingual delivery.

16. The antler composition according to claim 12, wherein said composition is produced by the following steps:
(a) mixing said β-cyclodextrin, said higher ester compound, said proteinase inhibitor, and said organic solvent with a specific ratio, adding said mixture into pure water, and blending them at room temperature for 18 to 36 h;
(b) adding an antler extract mixture to the mixture obtained from step (a), and blending the mixture with low speed at room temperature for 18 to 24 h;
(c) incubating the mixture at 4° C. for 24 to 48 h until precipitate performs; and
(d) filtering said mixture to obtain the precipitate.

17. The antler composition according to claim 16, further comprising adding 3 fold of water to the final product, mixing well, sterilizing and packing the product with a spray aerosol suitable for nasal or sublingual delivery.

* * * * *